US00PP32883P2

(12) United States Plant Patent
Ruter

(10) Patent No.: US PP32,883 P2
(45) Date of Patent: Mar. 9, 2021

(54) ***HIBISCUS* PLANT NAMED 'RUTHIB3'**

(50) Latin Name: *Hibiscus moscheutos*
Varietal Denomination: RutHib3

(71) Applicant: University of Georgia Research Foundation, Inc., Athens, GA (US)

(72) Inventor: John M. Ruter, Bishop, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 16/602,705

(22) Filed: Nov. 22, 2019

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./257
CPC ... A01H 5/02; A01H 5/00; A01H 6/60; A01H 6/608
See application file for complete search history.

(56) References Cited

U.S. PATENT DOCUMENTS

PP11,854 P2 * 5/2001 Fleming ..... A01H 5/02 Plt./257
PP32,036 P2 * 8/2020 Hansen ..... A01H 5/02 Plt./257

OTHER PUBLICATIONS

Issuu 2020 Star Roses and Plants Catalog, retrieved on Jun. 2, 2020, retrieved from the Internet at https://issuu.com/starrosesandplants/docs/2020_starrosesandplants_catalog, cover page, pp. 6,139,161. (Year: 2019).*

* cited by examiner

*Primary Examiner* — June Hwu
(74) *Attorney, Agent, or Firm* — Klarquist Sparkman, LLP

(57) ABSTRACT

A new *Hibiscus* plant named 'RutHib3' is characterized by a combination of good form, medium vigor, green/reddish foliage, magenta flowers with a red-purple eye, and good tolerance of *Hibiscus* sawfly and leaf spot pathogens.

3 Drawing Sheets

Genus and species: *Hibiscus moscheutos*.

Variety denomination: The new *Hibiscus moscheutos* claimed is of the cultivar denominated 'RutHib3'.

BACKGROUND OF THE INVENTION

The present invention relates to a new and distinct cultivar *Hibiscus moscheutos*, botanically known as *Hibiscus moscheutos* 'RutHib3'.

The new *Hibiscus moscheutos* 'RutHib3' is a product of a planned breeding program conducted by the Inventor at a horticulture farm in Watkinsville, Ga. The objective of the *Hibiscus* breeding program is to create new plant cultivars with ornamental leaf distinctions, abundant flowers, and tolerance to insects and pathogens.

The new *Hibiscus moscheutos* 'RutHib3' is a product of (*Hibiscus moscheutos* subsp. *moscheutos* x *H. moscheutos* subsp. *lasiocarpos* Hib2015-58) x *Hibiscus moscheutos* subsp. *moscheutos* 'RutHib4' (Inventor controlled crosses, not patented). The cross was made in 2017. 'RutHib3' has been evaluated through trials at a horticulture farm in Watkinsville, Ga. from spring of 2018 and the plant 'RutHib3' was selected in 2018.

Asexual reproduction of the new *Hibiscus moscheutos* 'RutHib3' was by vegetative terminal cuttings in a controlled environment in Watkinsville, Ga. since 2019. These observations have shown that the unique features of this new *Hibiscus moscheutos* 'RutHib3' are stable and have reproduced true to type in successive generations.

SUMMARY OF THE INVENTION

The cultivar 'RutHib3' has not been observed under all possible environmental conditions. The phenotype may vary somewhat with variations in environment and cultural practices such as temperature and light intensity without, however, any variance in genotype.

The following describes the distinguishing characteristics of the new *Hibiscus moscheutos* cultivar named 'RutHib3'. The following traits set 'RutHib3' apart from the male parent 'RutHib4' and the female parent, which is no longer available: 'RutHib3' has a compact and rounded form, medium vigor, green/reddish foliage, magenta flowers, and good tolerance to *Alternaria alternata, Cercospora*, and *Hibiscus* sawfly. In addition, 'RutHib3' can be distinguished from related known cultivars having pink flowers with a red eye and reddish green foliage, for example 'Dark Mystery' (U.S. Plant Pat. No. 32,036 P2) or 'Plum Crazy' (U.S. Plant Pat. No. 11,854 P2). 'Dark Mystery' has a white petal with pink coloration coming from streaking originating at the central eye. 'Plum Crazy' has plum/purple petals with darker streaking from the central eye. In contrast, 'RutHib3' has solid magenta petals with no streaking. Both 'Dark Mystery' and 'Plum Crazy' have dissected or maple-cut foliage, while 'RutHib3' has limited to no lobing. The foliage of 'Dark Mystery' and 'Plum Crazy' is described as slightly lustrous and some luster, respectively, and both are glabrous. In contrast, 'RutHib3' foliage sheen is matte, not lustrous, and has stellate pubescence.

BRIEF DESCRIPTION OF THE FIGURES

The accompanying colored photographic illustrations show the overall appearance and distinct characteristics of the new cultivar of *Hibiscus moscheutos* 'RutHib3'. The colors in the photograph are as close as possible with the photographic and printing technology utilized.

DETAILED BOTANICAL DESCRIPTION

Figure 1:
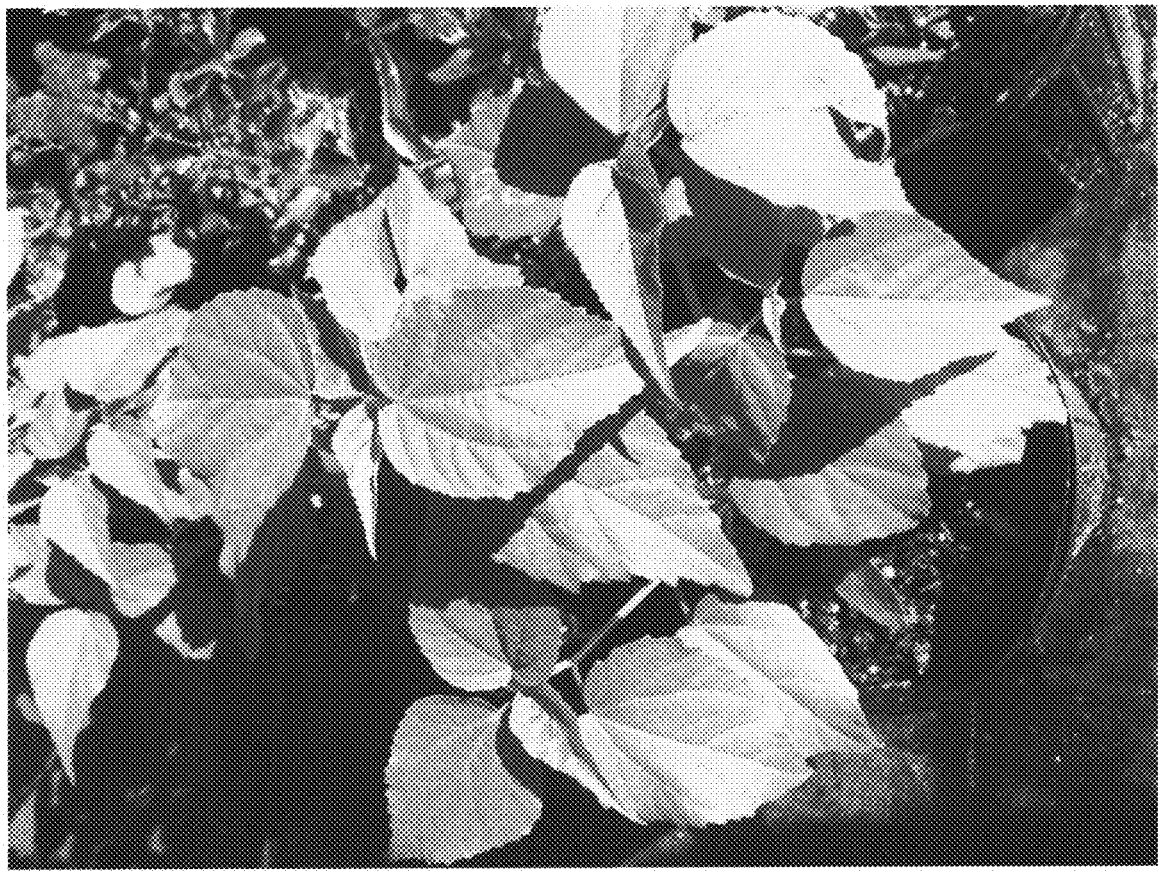
FIG. 1 is a photograph of a plant of the new 'RutHib3' variety showing its green foliage.
Figure 2:
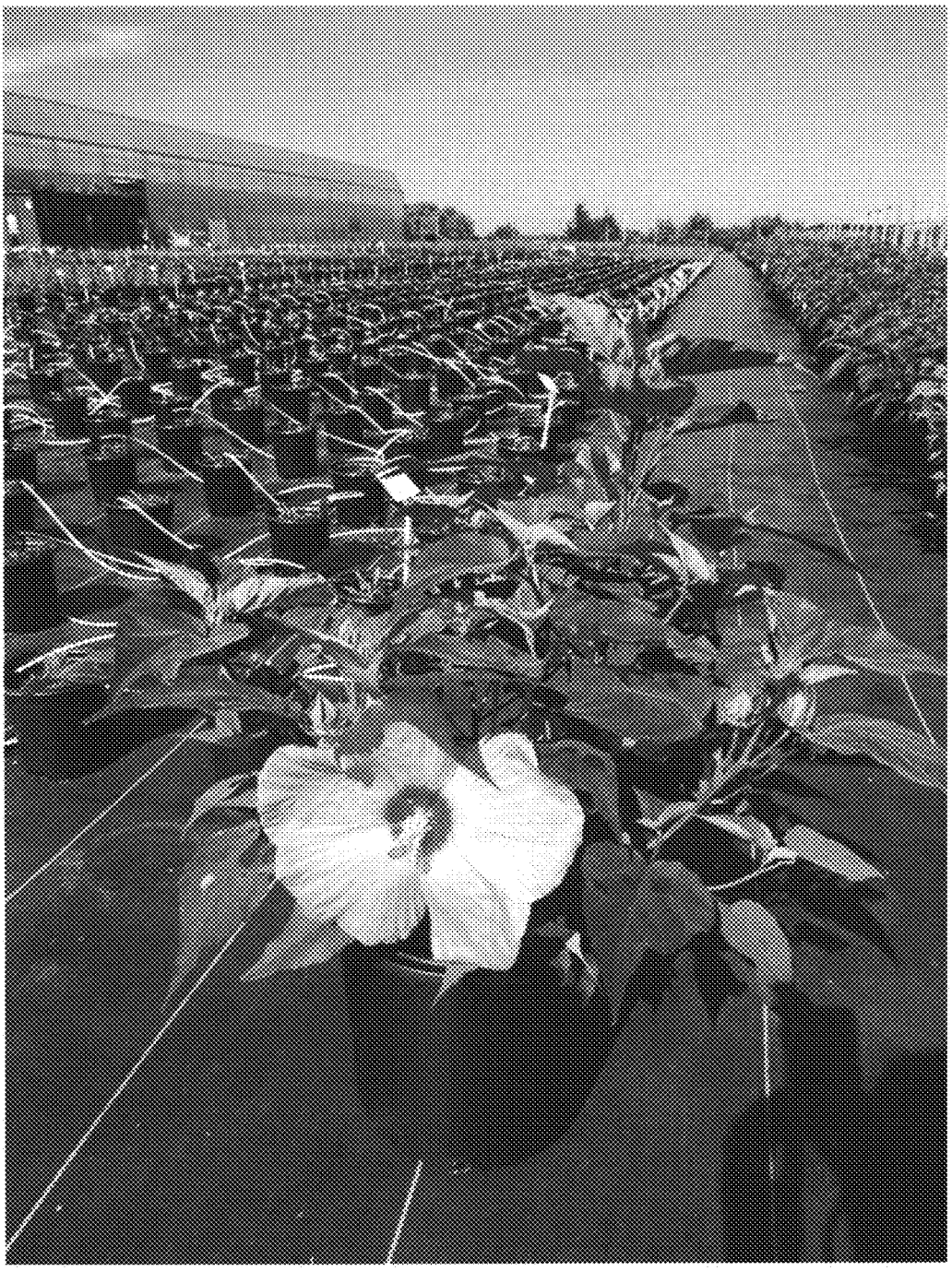
FIG. 2 is a photograph of a plant of the 'RutHib3' variety with flowers; the plant in this photograph is 11 months old from an unrooted cutting.
Figure 3:
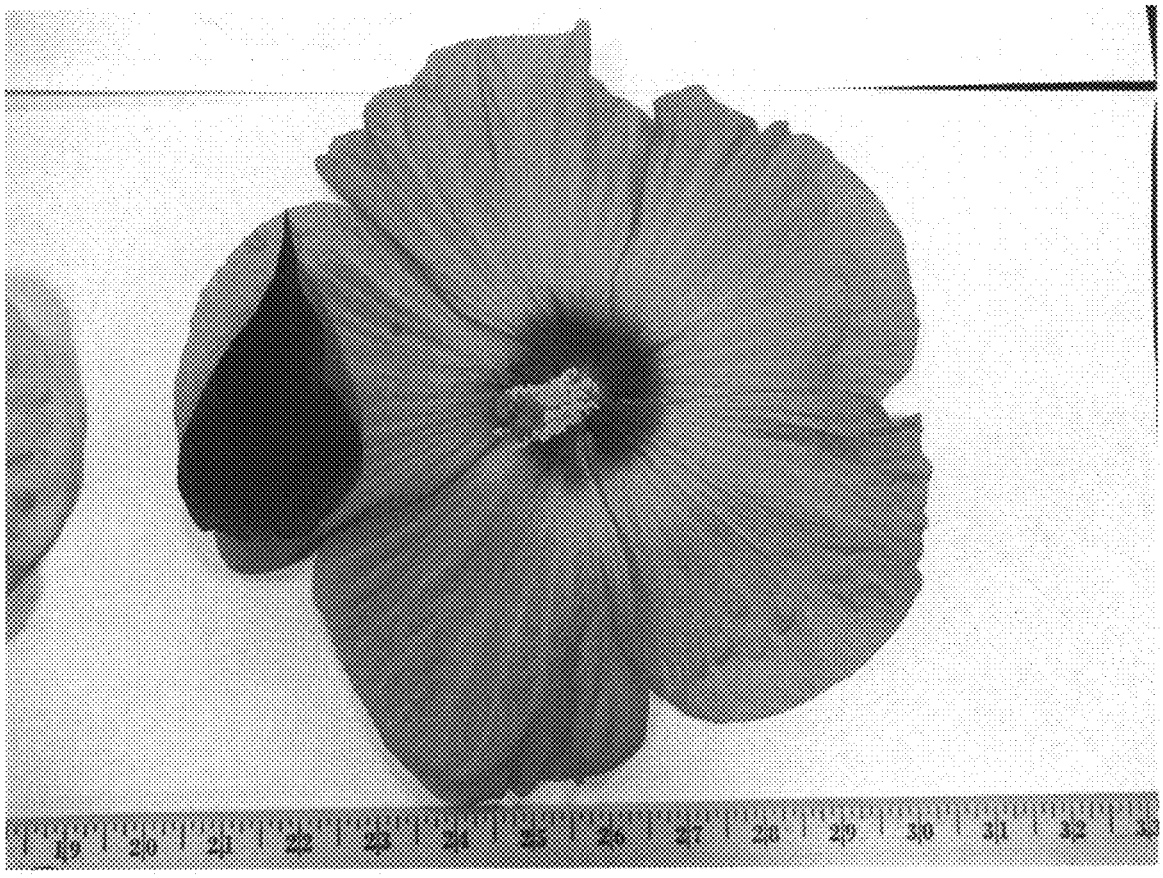
FIG. 3 is a close up photograph of a flower and a leaf with darker coloration of the plant of FIG. 2.

The following is a detailed description of the *Hibiscus moscheutos* cultivar named 'RutHib3'. Data was collected at a horticulture farm in Watkinsville, Ga. from a two-year old plant grown outdoors and planted in the ground.

The color determination is in accordance with The R.H.S. Colour Chart, $6^{th}$ edition published in 2015 by The Royal Horticultural Society (R.H.S.), London, England, except where general color terms of ordinary significance are used.

Habit: Compact, rounded.

Size of plant:

A. *Height.*—81 cm.

B. *Width.*—119 cm.

Stem:

A. *Color.*—Yellow-Green 144B.

B. *Length.*—85 cm.

C. *Diameter.*—1.5-2 cm (base) 0.75-1 cm (mid stem).

D. *Pubescence.*—None.

E. *Shape.*—Round.

F. *Odor* (*of bruised stem*).—None.

G. *Internode length.*—3-6.5 cm.

Leaf:

A. *Color* (*R.H.S.*).—1. Upper: Green NN137B or Greyed-Purple N186C when under high intensity sunlight or as the foliage matures. 2. Lower: Yellow-Green 148B.

B. *Mature size* (*l*×*w*).—11 cm×5.5 cm.

C. *Apex.*—Acute.

D. *Base.*—Cordate.

E. *Margin.*—Crenate to dentate.

F. *Shape.*—Ovate.

G. *Number of lobes.*—0.

H. *Pubescence.*—Both upper and lower are heavily stellate.

I. *Arrangement on stem.*—Alternate.

J. *Venation.*—Palmate.

K. *Texture.*—Soft, velvety.

Petiole:

A. *Length:* 4-6.5 cm.

B. *Shape.*—Oval.

C. *Color.*—1. Upper: Greyed-Red 178A. 2. Lower: Yellow-Green 144C.

D. *Pubescence.*—Moderately stellate.

E. *Diameter.*—2-3 mm.

Flower:

A. *Inflorescence.*—1. Flowers per stem: 1; Occur in terminal clusters of 5 to 10 flowers per cluster.

B. *Individual flower.*—1. Axillary, terminal: Axillary. 2. Symmetry: Actinomorphic. 3. Petals — a. Size (L×W) — 10-12 cm×10-12 cm. b. Shape — Obovate. c. Apex — Round. d. Base — Truncate. e. Margin — Entire. f. Color at peak of bloom — 1. Upper — Red-purple 64C, 59A eye. 2. Lower — Red-purple 64C, 59A eye. g. Size of eye zone — Small. h. Petal undulation — Weak. i. Petal arrangement — Slightly overlapping. j. Flower lastingness — Flowers open before dawn and close by late afternoon on a sunny day. 4. Pedicels — a. Color (R.H.S.) — Yellow-Green 144C with a splash of Greyed-Purple 183C along one side. b. Pubescence — Moderately stellate. c. Length — 4.5- 5.5 cm. 5. Sepals — a. Number — 5. b. Size (L×W) — 4×2 cm. c. Shape — Ovate. d. Pubescence — Both inner and outer are heavily stellate. e. Color (R.H.S.) — 1. Outer — Yellow-Green 146C. 2. Inner — Yellow-Green 144B. 6. Stamens — a. Number — 100-200. b. Size — (L×W). 1. Anther — 3 mm×2 mm. 2. Filament — 3.5 mm×0.5 mm. c. Color — 1. Anther — Greyed-Yellow 160D. 2. Filament — Red-Purple 68A at base; Red-Purple 68D at top. d. Pollen Color — Greyed-Yellow 160C. e. Pubescence — 1. Anther — Smooth. 2. Filament — Essentially smooth-has the occasional solitary papillose-hispid hair. f. Staminal column — 5-6 mm. 7. Pistils — a. Number — 5. b. Size (L×W) — 1. Style — 10-12 mm×1 mm. 2. Ovary — 7 mm×7 mm. c. Color of Style (R.H.S.) — Red-Purple 67A. d. Color of Stigma (R.H.S.) — White 155B covered with hairs that are Red-Purple 65A. e. Color of Ovary (R.H.S.) — Yellow-Green 150D. 8. Bracts — a. Number — 10-15. b. Size — 25-30 mm×2-3 mm. c. Color (R.H.S.) — 1. Inner — Yellow-Green 146C. 2. Outer — Yellow-Green 146B with Greyed-Purple 187A at tip. 9. Flower bud — a. Average length — 3 cm. b. Color — Yellow-green 144A.

Fruit and seed: None.

Winter Hardiness not determined. Has been grown in Watkinsville, Ga.; USDA hardiness zone 8a.

Good tolerance of *Hibiscus* sawfly (*Atomacera decepta*). Good tolerance of leaf spot pathogens (*Alternaria alternata* and *Cercospora*).

What is claimed is:

1. A new and distinct cultivar of the *Hibiscus* plant named 'RutHib3' as illustrated and described herein.

* * * * *